United States Patent [19]
Ouchi

[11] Patent Number: 6,001,114
[45] Date of Patent: Dec. 14, 1999

[54] OPERATIVE INSTRUMENT FOR ENDOSCOPIC SURGERY

[75] Inventor: Teruo Ouchi, Saitama, Japan

[73] Assignee: Asahi Kogaku Kogyo Kabushiki Kaisha, Tokyo, Japan

[21] Appl. No.: 09/072,027

[22] Filed: May 5, 1998

[30] Foreign Application Priority Data

May 7, 1997 [JP] Japan .................................. 9-116603

[51] Int. Cl.⁶ .................................................. A61B 17/32
[52] U.S. Cl. ........................................... 606/167; 606/170
[58] Field of Search .................................. 606/170, 180, 606/167, 205, 206; 604/72

[56] References Cited

U.S. PATENT DOCUMENTS

| | | |
|---|---|---|
| 3,960,143 | 6/1976 | Terada . |
| 4,807,593 | 2/1989 | Ito . |
| 4,889,106 | 12/1989 | Watanabe . |
| 5,501,654 | 3/1996 | Failla et al. . |
| 5,593,416 | 1/1997 | Donahue . |
| 5,643,294 | 7/1997 | Tovey et al. ............................ 606/170 |
| 5,683,413 | 11/1997 | Miyagi .................................... 606/170 |
| 5,741,286 | 4/1998 | Recuset ................................... 606/170 |

FOREIGN PATENT DOCUMENTS

| | | |
|---|---|---|
| 0598461 | 5/1994 | European Pat. Off. . |
| 8140981 | 6/1996 | Japan . |

*Primary Examiner*—Michael Buiz
*Assistant Examiner*—Kevin Truong
*Attorney, Agent, or Firm*—Greenblum & Bernstein, P.L.C.

[57] ABSTRACT

An operative instrument for endoscopic surgery which can be used in combination with a normal, straight trocar. The operative instrument for endoscopic surgery includes a jacket tube (11), which is formed from an elastic tubular member to normally maintains a curved shape and can be elastically deformed to be insertable into a straight, cylindrical trocar (1), a manipulating shaft (27), which is elastic, has a distal end operative member (24) connected to the distal end thereof for performing a treatment within the body, and is passed through the jacket tube (11), and a manipulating part (30), which is connected to the proximal side of the jacket tube (11) for manipulating the distal end operative member (24) via manipulating shaft (27).

12 Claims, 8 Drawing Sheets

OPERATIVE INSTRUMENT FOR ENDOSCOPIC SURGERY

BACKGROUND OF THE INVENTION

The present invention concerns an operative instrument for endoscopic surgery, which is passed through a tubular trocar and is used to perform a surgical procedure, etc. inside a body cavity under endoscopic observation.

In recent years, endoscopic surgery has come to be performed widely for various types of surgery since the interior of the body cavity can be subjected to surgical treatment without large incision. In the endoscopic surgery, several small opened parts are made in the abdominal wall, a tubular trocar is passed through each opened part, and an endoscope is passed through one trocar while various operative instruments are passed through the other trocars.

The use of the trocars prevents damage of the opened part of the abdominal wall in the process of inserting or removing the endoscope and operative instrument, and prevents leakage of air when operative instruments are used interchangeably.

The length of an operative instrument used in the surgery under endoscopic observation is short since it is to be used upon insertion through a trocar. In general, the operative instrument is designed such that manipulating shaft (or manipulating wire) is retractably inserted and positioned in the axial direction in a rigid jacket tube, and a distal end operative member, which is actuated by advancing and retreating the manipulating shaft, is attached to the distal end of the jacket tube.

In case where the rear side of an organ must be subjected to treatment by endoscopic surgery, an operative instrument with a curved jacket tube is used.

Since the operative instrument is used upon being passed through the trocar as abovementioned, a trocar with a curvature which matches the curvature of the jacket tube must be prepared.

SUMMARY OF THE INVENTION

Thus, the object of the present invention is to present an operative instrument for endoscopic surgery with which various procedures can be performed readily under endoscopic observation using a normal, straight trocar.

To attain the above-noted object, the present invention provides an operative instrument for endoscopic surgery with a jacket tube which is elastically deformable but normally maintains a curved state. Since the jacket tube, that normally maintains a curved state, is inserted into a straight trocar while being deformed elastically so that the jacket tube will return to the curved condition upon protruding to a portion inside the body from the distal end of the trocar, various procedures under endoscopic observation can be performed readily on portions at the rear side of an organ, etc.

The jacket tube normally maintains a curved shape but can present a straight form if an external force is applied thereto. The external force means a force that acts on the jacket tube when the jacket tube is inserted into a straight, rigid trocar.

In a preferable embodiment, an operative instrument for endoscopic surgery comprises a jacket tube, which is formed from an elastic tubular member to have a curved form in the normal or natural state and can be elastically deformed to be removably inserted into a straight, cylindrical trocar, a manipulating shaft, which is elastic, has a distal end operative member connected to the distal end thereof for performing a treatment within the body, and is passed through the jacket tube, and a manipulating part, which is connected to the proximal side of the jacket tube for manipulating the distal end operative member via the manipulating shaft.

The manipulating shaft may be formed to have a curved form in the normal or natural state that matches the curvature of the jacket tube, and the manipulating shaft may be formed from a pipe-like member.

Also, the manipulating shaft may be removably inserted into the jacket tube and the manipulating part may be removably attached to the jacket tube and the manipulating shaft. Furthermore, the jacket tube may be rotatable about the axis with respect to the manipulating part.

The present disclosure relates to the subject matter contained in Japanese patent application No. Hei. 9-116603 (filed on May 7, 1991) which is expressly incorporated herein by reference in its entirety.

BRIEF DESCRIPTION OF THE DRAWINGS

Each of FIGS. 7A and 7B is a schematic, sectional view showing how a jacket tube part and a manipulating shaft are coupled to a manipulating part.

DETAILED DESCRIPTION OF THE OPERATIVE INSTRUMENT FOR ENDOSCOPIC SURGERY

An operative instrument for endoscopic surgery will now be described with reference to the drawings.

Figure 1:
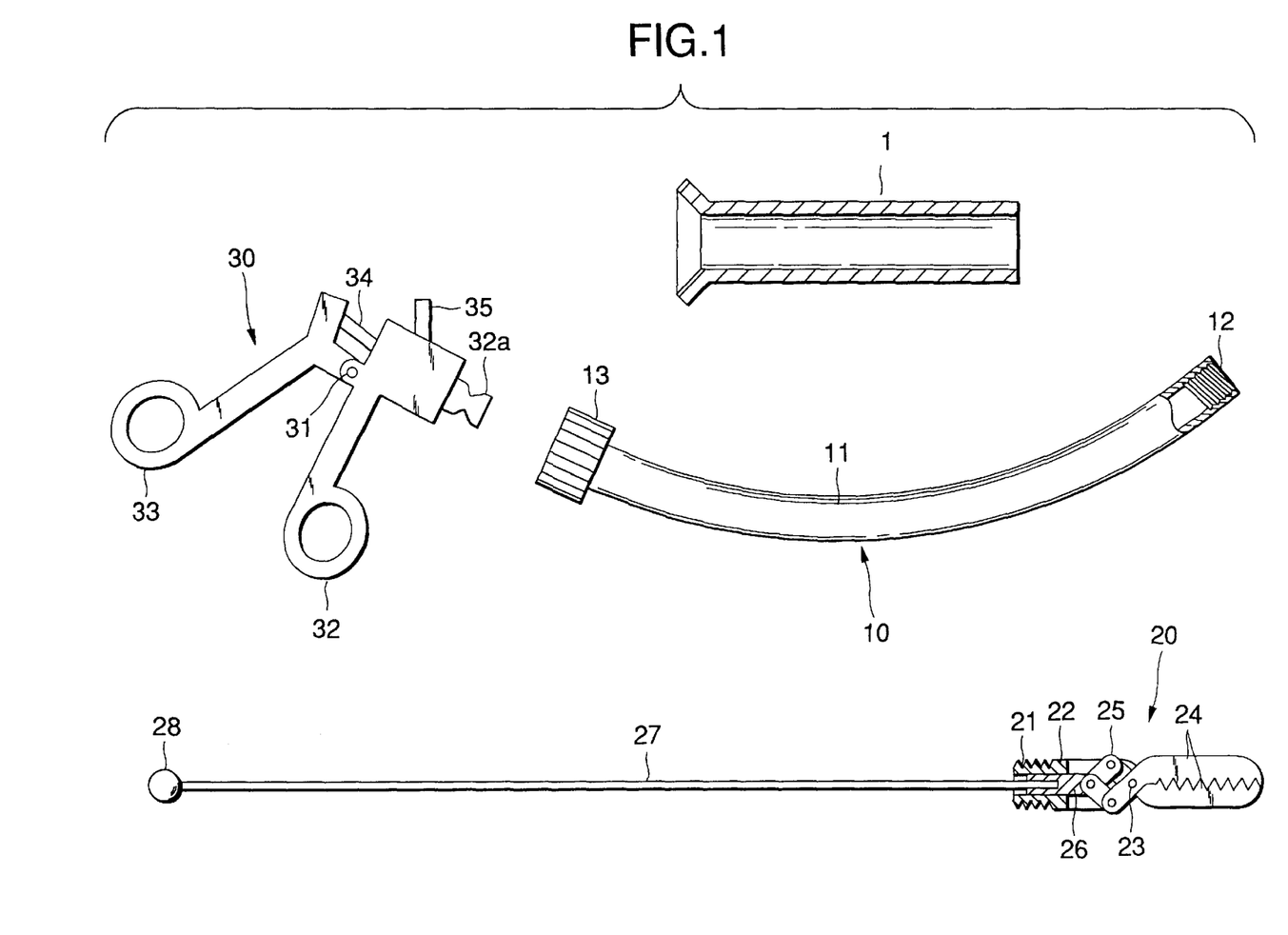
FIG. 1 is an exploded view of an operative instrument for endoscopic surgery of an embodiment.
Figure 2:
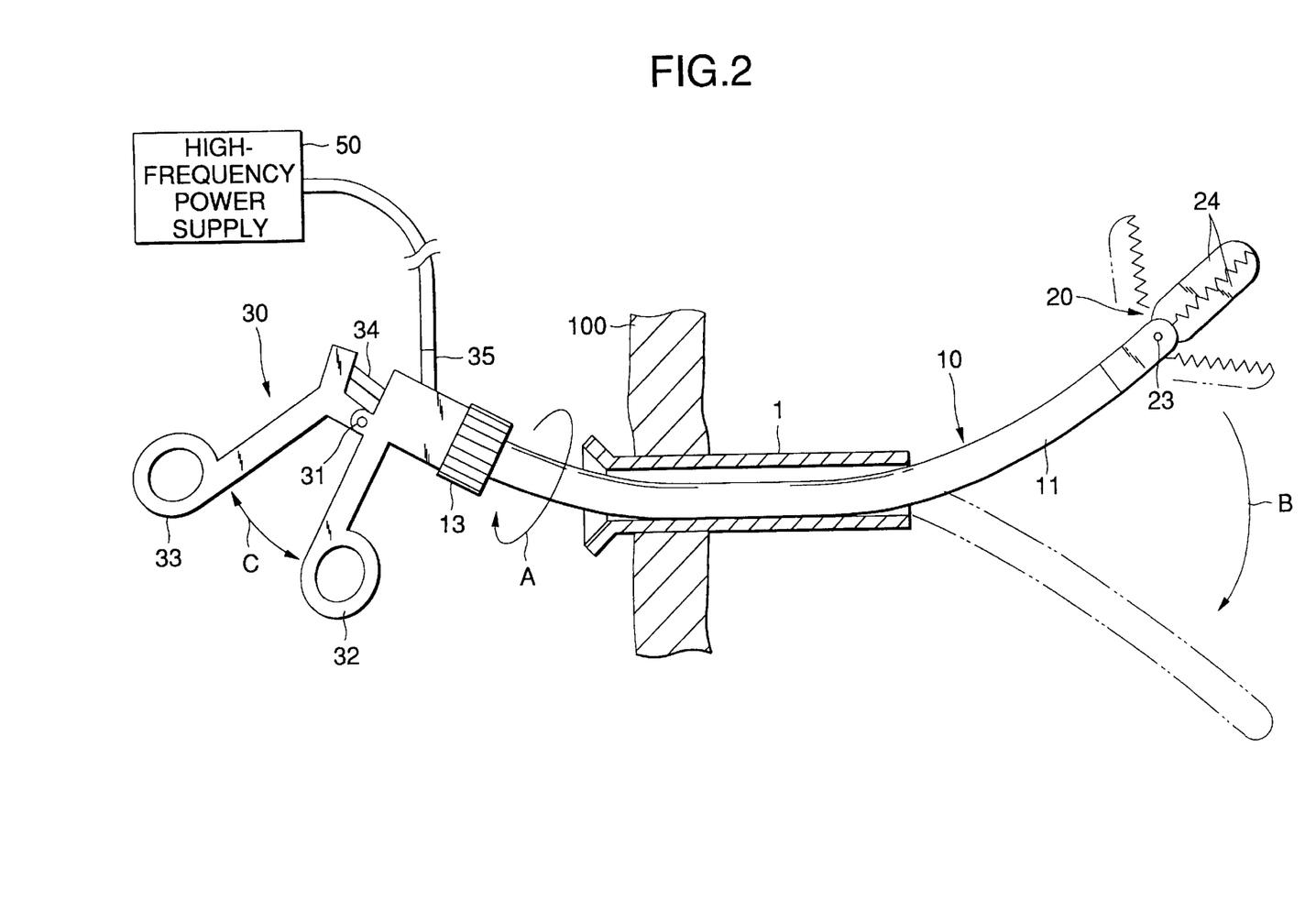
FIG. 2 is an overall arrangement diagram of the condition of use of the operative instrument for endoscopic surgery of the embodiment.

FIGS. 1 and 2 show an operative instrument for endoscopic surgery which is used as a retention forceps, with FIG. 2 showing the condition of use and FIG. 1 showing the condition where the retention forceps has been disassembled into the respective parts.

A straight, tubular (so-called direct) trocar 1 is formed from rigid metal or plastic material and is passed through a small hole or opened part opened in a body wall 100.

The insertion entrance at the proximal side of the trocar 1 is enlarged to have a tapered shape so that the operative instrument can be inserted readily. The trocar 1 may also be formed from an elastic material so that it may bend.

The operative instrument for endoscopic surgery includes a jacket tube part 10 which is inserted through the trocar 1, an operative mechanism part 20 which is disposed at the distal end of jacket tube part 10 to perform a treatment on a diseased part inside the body, and a manipulating part 30 which is disposed at the proximal end of the jacket tube part 10 to remotely manipulate the operative mechanism part 20.

The jacket tube part 10 is formed from a flexible and elastically deformable jacket tube 11, and has a female thread 12 on the inner peripheral face of the distal end. The female thread 12 is used to couple the jacket tube part 10 with the operative mechanism part 20. A coupling ring 13 is attached to the proximal end of the jacket tube part 10 to couple the jacket tube part 10 with the manipulating part 30.

The jacket tube 11 is formed, for instance, of fluoroplastic, nylon, or polyimide resin so that the jacket tube 11 normally maintains a curved shape. The degree of curvature is selected according to the purpose of use, etc.

The operative mechanism part 20 includes a distal end body 22 having a male thread 21 that can be detachably screwed into the female thread 12 of jacket tube part 10, a pair of distal end retention pieces 24 (distal end operative member) on the distal end body 22, that opens and closes about a pivot 23, and a link mechanism 25 on the distal end body 22, that converts a linear motion of a coupling shaft 26 into the opening and closing motion of the distal end retention pieces 24. The distal end of a manipulating shaft 27, which is passed through the jacket tube part 10 entirely, is coupled to the link mechanism 25 via the coupling shaft 26.

Figure 7A:
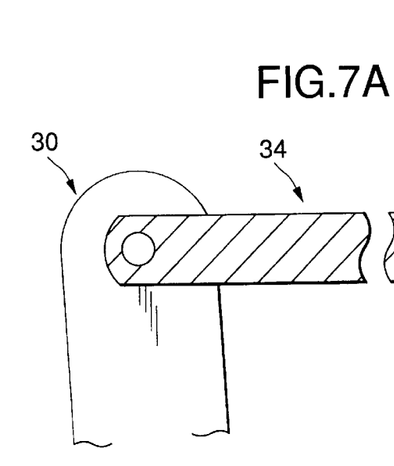
Figure 7B:
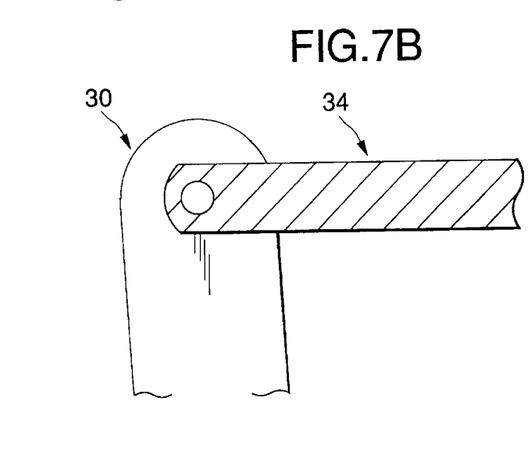
Figure 7C:
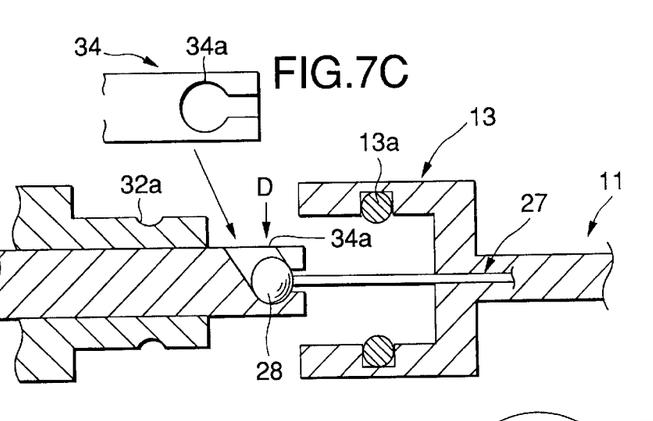
FIG. 7C is a partial view showing the key-shaped slit.
Figure 7D:
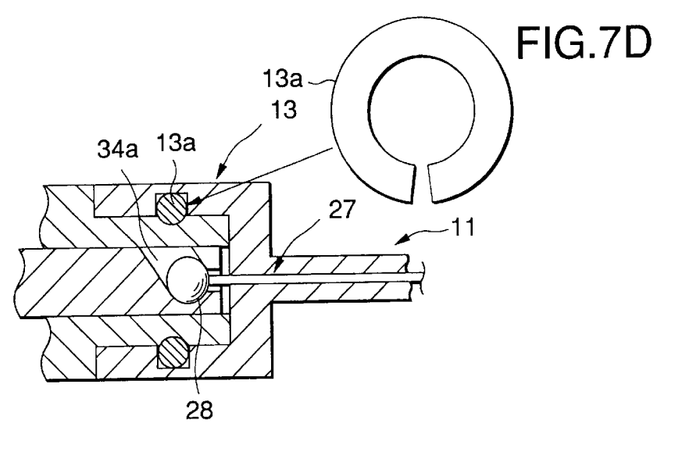
FIG. 7D is an enlarged view of the annular elastic member.

The manipulating shaft 27 normally has a straight shape, but is elastically deformable to bend in conformity with the curvature of the jacket tube 11. To this end, the manipulating shaft 27 is formed, for example, from an elastic stainless steel pipe. During use the manipulating shaft 27 is positioned inside of the jacket tube 11 and axially movably arranged with respect to the jacket tube 11. A coupling end 28 on the proximal end of the manipulating shaft 27 is coupled to the manipulating part 30 in such a manner as to permit relative rotation of the manipulating shaft 27 with respect to the manipulating part 30. If the coupling ring 13 is rotated, the jacket tube part 10 and the operative mechanism part 20 are rotated relative to the manipulating part 30. A distal end of an actuation shaft 34 of the manipulating part 30 is formed with a key-shaped slit 34*a* which permits insertion of the coupling end 28 together with a portion of the manipulating shaft 27 in the vicinity of the coupling end 28 into the inside of the actuation shaft 34 in a direction of an arrow D in FIG. 7A, and which retains the coupling end 28 in the inside of the actuation shaft 34 upon insertion as shown in FIG. 7B. Further, a partially-cut-away (C-shaped) annular elastic member 13*a* is provided on the inside of the coupling ring 13 so that the coupling ring 13 is elastically fitted in and engaged with an annular recess 32*a* formed on a protruded portion of a manipulating handle 32 when the protruded portion of the manipulating handle 32 is inserted into the coupling ring 13 in place as shown in FIG. 7B.

Figure 8:
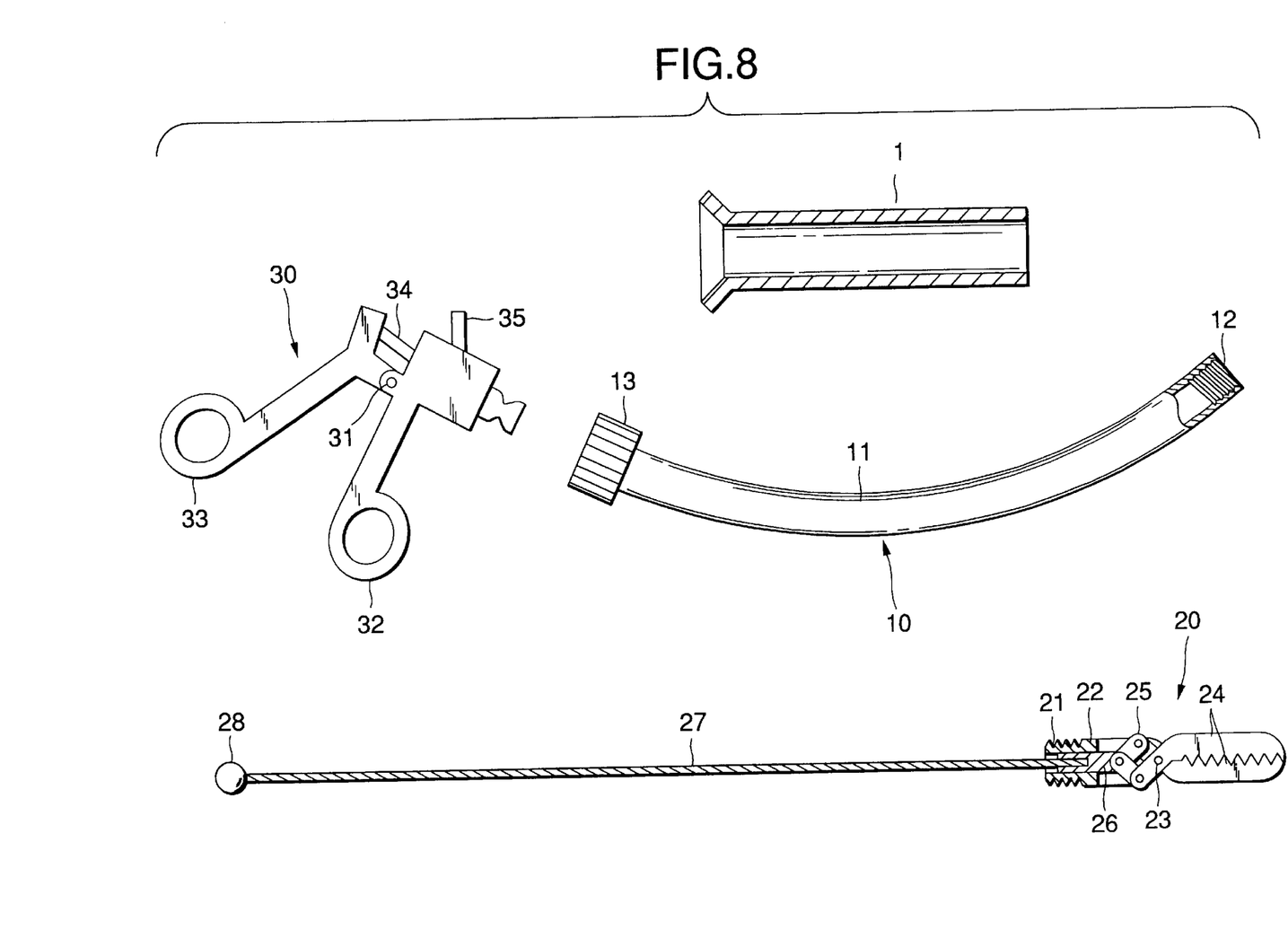
FIG. 8 is an exploded view of an operative instrument for endoscopic surgery, in which a manipulating shaft of a stranded wire is used.

The manipulating shaft 27 may be formed from a pipe or bar made of a slightly hard plastic material such as fluoroplastic or nylon, or may be formed from a stranded wire with excellent resistance against compression as shown in FIG. 8.

Figure 3:
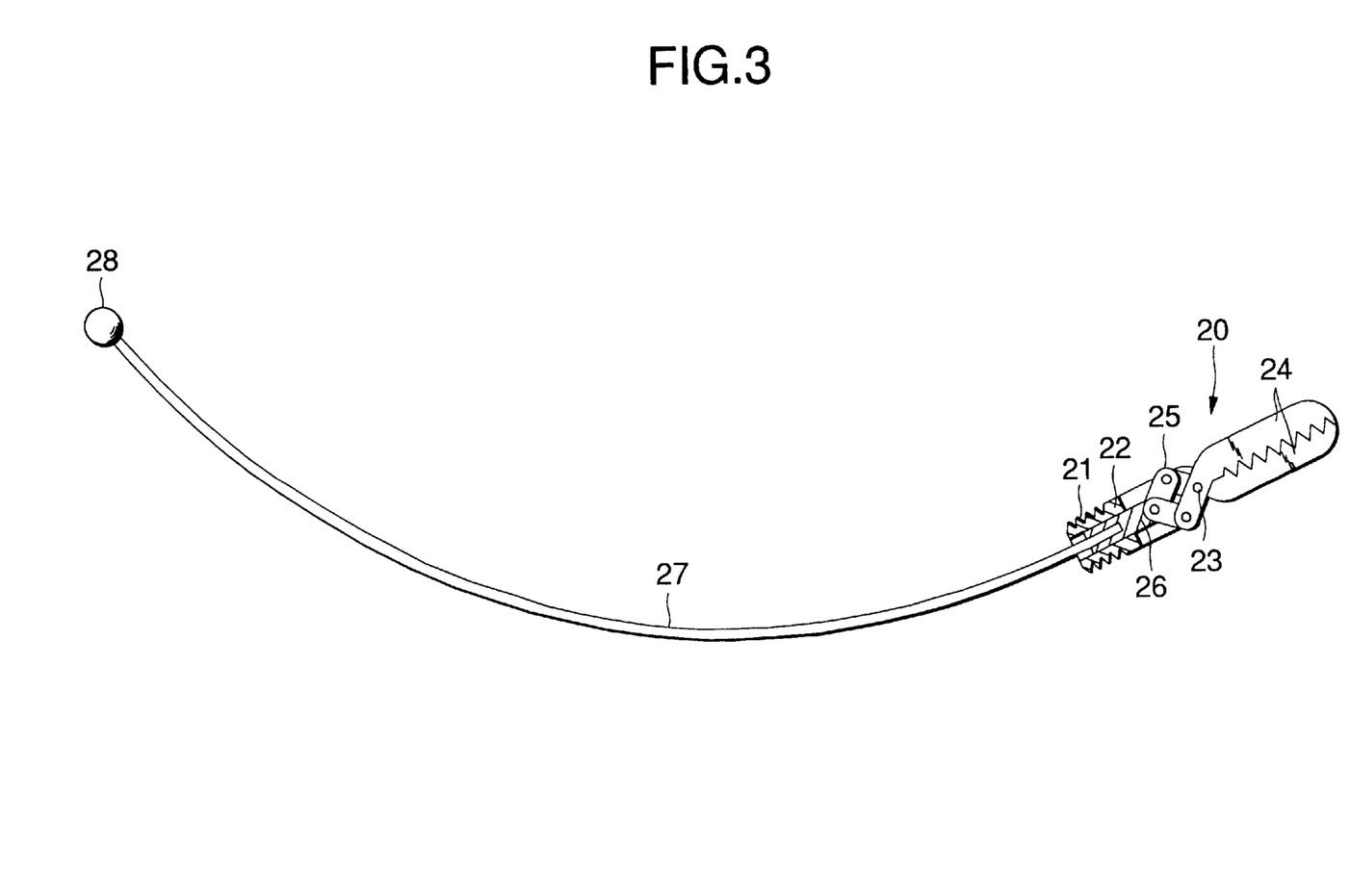
FIG. 3 is a diagram showing a partial arrangement of an example in which a curved manipulating shaft is used.

Also as shown in FIG. 3, the manipulating shaft 27 may be formed to normally maintain a curved shape to match the curved shape of the jacket tube 11. The distal end retention pieces 24, the link mechanism 25, etc. are members that differ according to the type of operative instrument. That is to say, members that constitute the operative mechanism part 20 can be arranged or modified in various manner depending on a required function of operative instrument. The coupling of operative mechanism part 20 and jacket tube 11 is not limited to threaded engagement but may also be accomplished by other connection mechanisms such as a bayonet coupling mechanism and a click mechanism.

Returning to FIGS. 1 and 2, the manipulating part 30 is provided with a pair of manipulating handles 32 and 33, which can be manipulated to rotate about a pivot 31, and by the manipulation of these handles 32 and 33, an actuation shaft 34, coupled to the coupling end 28 of the manipulation shaft 27, is driven in the axial direction.

If the operative instrument for endoscopic surgery with the above arrangement is to be used, the jacket tube 11, which normally maintains a curved shape, is passed through the straight trocar 1 while being elastically deformed. In the condition where jacket tube 11 has been passed through the trocar 1, the jacket tube 11 returns to the curved condition so that the operative mechanism part 20 is oriented in a direction away from the axis of the trocar 1 as shown in FIG. 2.

By rotating the jacket tube part 10 in the A direction about the axis with respect to the manipulating part 30 at the portion at which the jacket tube part 10 is coupled to manipulating part 30, a portion of the jacket tube 11 that protrudes from the distal end of the trocar 1 can be rotated along with the operative mechanism part 20 in the B direction, so that the orientation of the operative mechanism part 20 can be changed largely. That is to say, the rotation at that coupled portion is transmitted to the operative mechanism part 20 without any angular loss, and therefore the operative mechanism part 20 can be freely directed to the desired orientation.

When the manipulating handles 32 and 33 are manipulated in the directions of arrow C, the action of the manipulating handles 32 and 33 is transmitted from the actuation shaft 34 to the link mechanism 25 via the manipulating shaft 27, to thereby open or close the distal end retention pieces 24 to retain the target diseased part.

If a treatment using high-frequency current is to be required, a high-frequency power supply 50 is connected to a terminal 35 provided on the manipulating part 30 to supply high-frequency current with the operative mechanism part 20.

Figure 4:
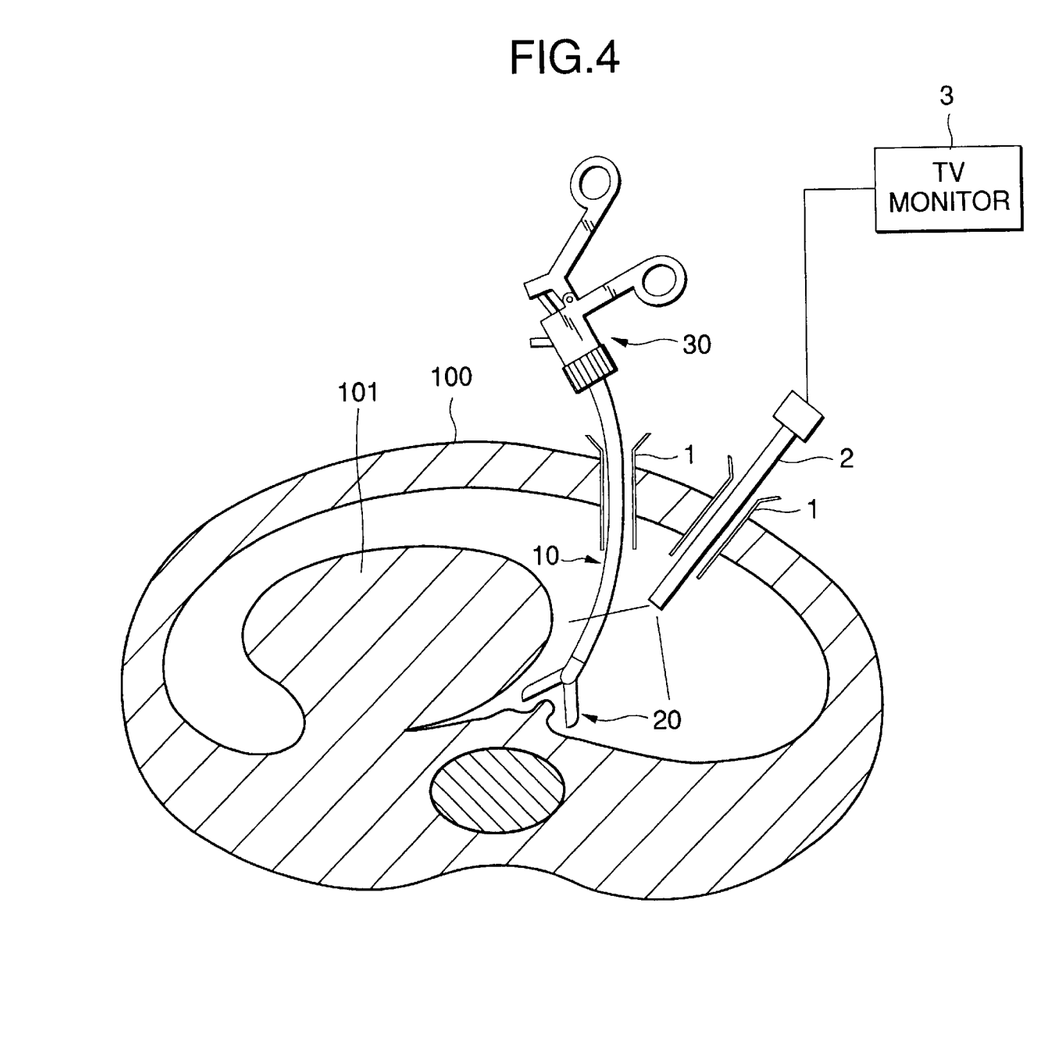
FIG. 4 is a schematic view of an example of endoscopic surgery with the operative instrument.
Figure 5:
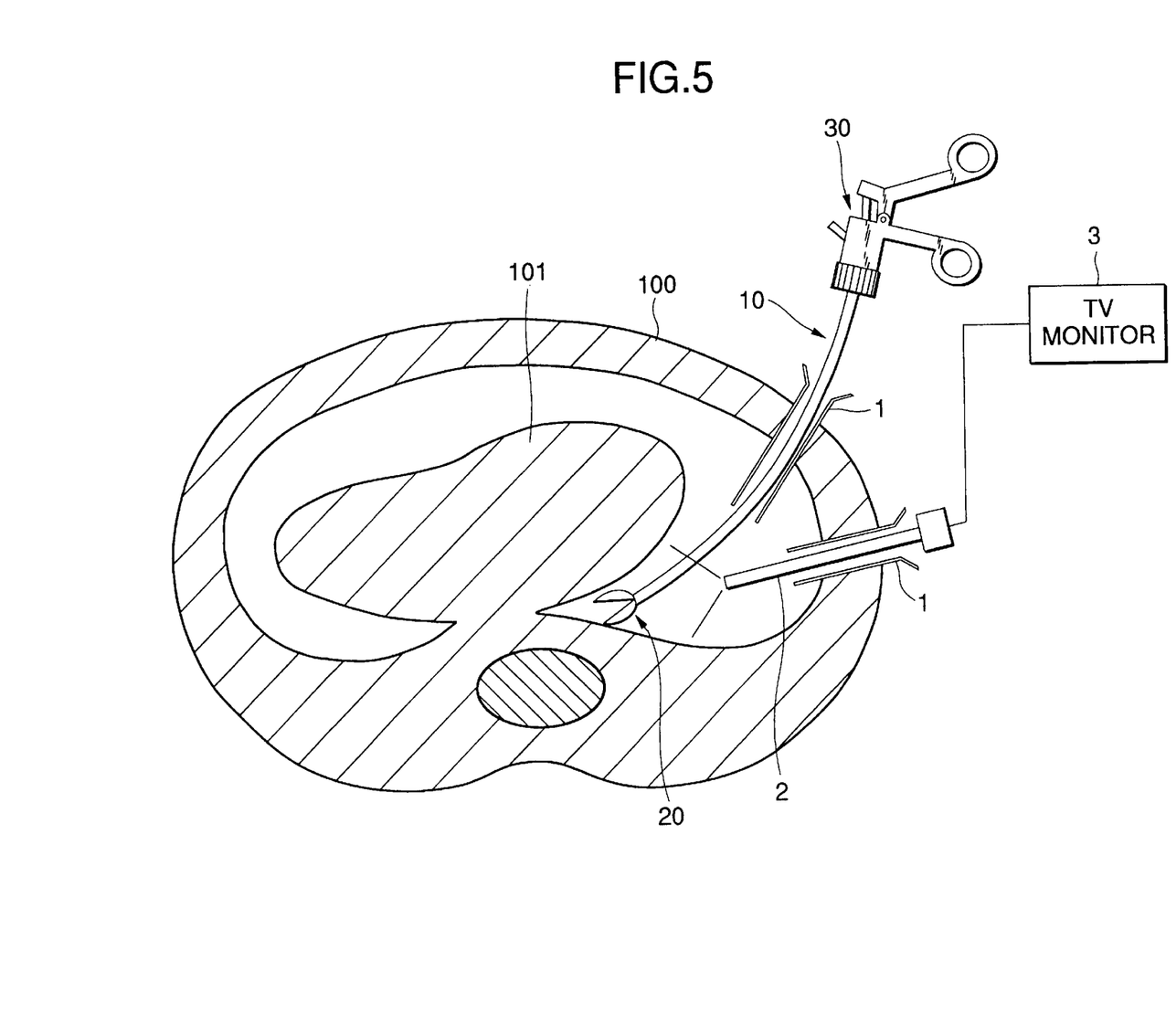
FIG. 5 is a schematic view of a second example of endoscopic surgery with the operative instrument.
Figure 6:
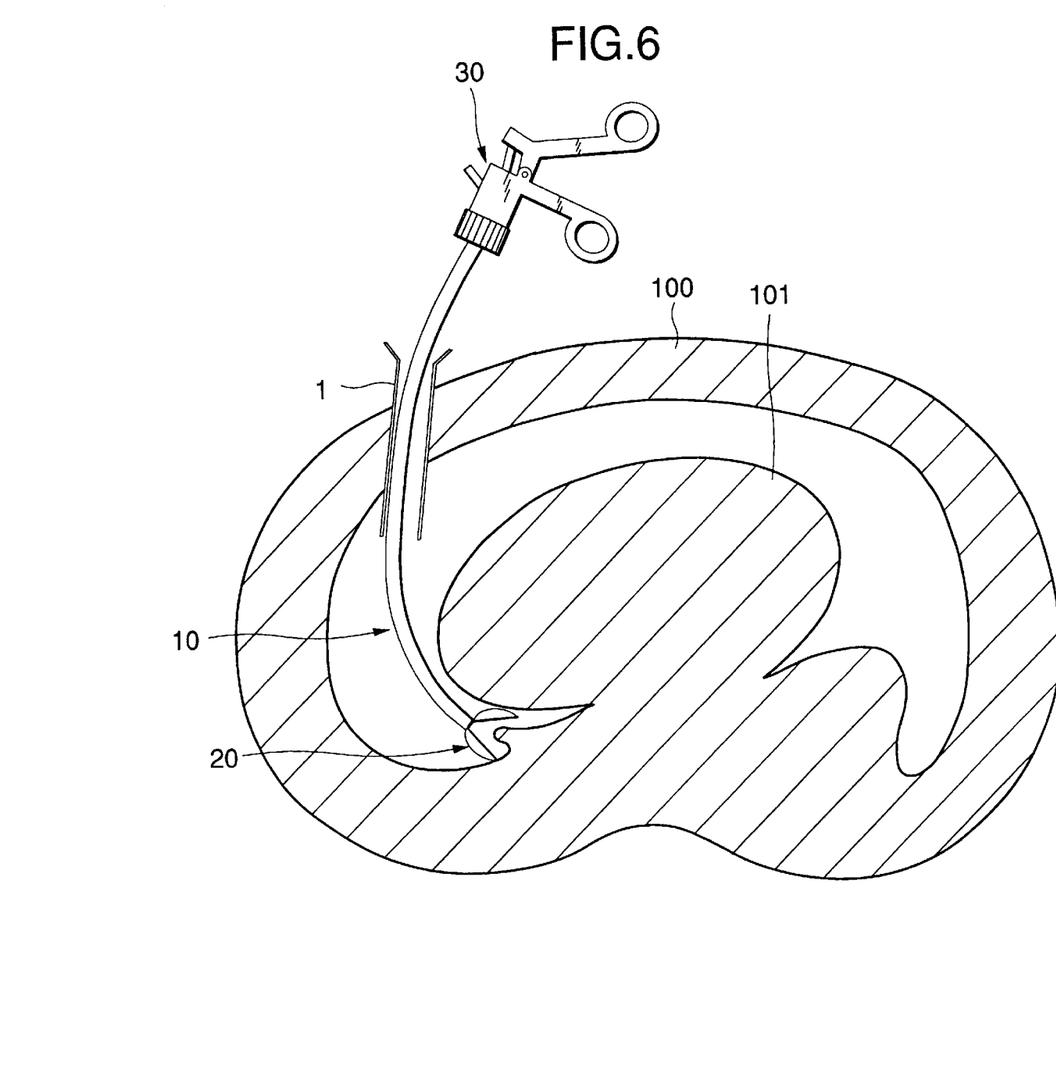
FIG. 6 is a schematic view of a third example of endoscopic surgery with the operative instrument.

By using the operative instrument for endoscopic surgery as constructed above, the distal end operative mechanism part 20 of the operative instrument can be guided readily via the straight trocar 1 to a portion located at the rear side of an organ 101 inside the body wall 100 to perform various procedures while viewing the observation image on a TV monitor 3 taken by an endoscope 2 passed through another trocar 1 as shown for example in FIGS. 4 and 5.

What is claimed is:

1. An operative instrument for endoscopic surgery in combination with a straight cylindrical trocar, said operative instrument comprising:

a flexible, elastically deformable tubular jacket tube normally maintaining a predetermined curved shape;

an elastic manipulating shaft passed through said jacket tube;

a distal end operative member connected to a distal end of said manipulating shaft for performing treatment within a body;

a manipulating part connected to a proximal end of said jacket tube for manipulating said distal end operative member via said manipulating shaft; and said tubular jacket tube passing through said straight cylinder trocar while being elastically deformed by said trocar, said jacket tube returning to the predetermined shape after passing through said trocar.

2. An operative instrument for endoscopic surgery as set forth in claim 1, wherein the manipulating shaft normally maintains a predetermined curved shape which matches said predetermined curved shape of said jacket tube.

3. An operative instrument for endoscopic surgery as set forth in claim 1, wherein said manipulating shaft is formed from a pipe-like member.

4. An operative instrument for endoscopic surgery as set forth in claim 1, wherein said manipulating shaft is removable from said jacket tube.

5. An operative instrument for endoscopic surgery as set forth in claim 1, wherein said manipulating part is removably connected to said jacket tube and said manipulating shaft.

6. An operative instrument for endoscopic surgery as set forth in claim 1, wherein said jacket tube is rotatable about an axis with respect to said manipulating part.

7. An operative instrument for endoscopic surgery as set forth in claim 6, wherein said manipulating shaft is rotatable about said axis with respect to said manipulating part so that said manipulating part is rotated together with said jacket tube.

8. An operative instrument for endoscopic surgery as set forth in claim 1, wherein said jacket tube is made of fluoroplastic, nylon or polyimide resin.

9. An operative instrument for endoscopic surgery as set forth in claim 1, wherein said manipulating shaft is formed from a stranded wire.

10. An operative instrument for endoscopic surgery as set forth in claim 1, wherein said distal end operative member is directly connected to a distal end of said jacket tube and said manipulating part is directly connected to said proximal end of said jacket tube.

11. An operative instrument for endoscopic surgery as set forth in claim 10, wherein said distal end operative member is directly connected to said distal end of said jacket tube by a threaded connection.

12. An operative instrument for endoscopic surgery as set forth in claim 10, wherein said manipulating part includes an annular recess and said proximal end of said jacket tube includes a coupling ring, said annular recess and coupling ring directly coupling said manipulating part to the other end of said jacket tube.

* * * * *